United States Patent [19]

Cooley

[11] Patent Number: 5,233,064
[45] Date of Patent: Aug. 3, 1993

[54] PREPARATION OF PALLADIUM CATALYSTS

[75] Inventor: Neil A. Cooley, Teddington, England

[73] Assignee: The British Petroleum Company, p.l.c., London, England

[21] Appl. No.: 866,645

[22] Filed: Apr. 9, 1992

[30] Foreign Application Priority Data

Apr. 13, 1991 [GB] United Kingdom ............... 9107887

[51] Int. Cl.$^5$ ............................................. C07F 15/00
[52] U.S. Cl. ........................................ 556/21; 556/136
[58] Field of Search ................................ 556/21, 136

[56] References Cited

FOREIGN PATENT DOCUMENTS 0121965 10/1984 European Pat. Off. .
0360359 3/1990 European Pat. Off. .

OTHER PUBLICATIONS

Knifton, Journal of Catalysis, vol. 60, pp. 27–40 (1979).

Primary Examiner—José G. Dees
Assistant Examiner—Porfirio Nazario
Attorney, Agent, or Firm—David J. Untener; Michael F. Esposito; David P. Yusko

[57] ABSTRACT

Palladium complexes having the general formula $Pd(R'CO_2)_2X$ where $R'$ is $C_1$ to $C_{10}$ alkyl or $C_6$ to $C_{10}$ aryl and X is a chelating ligand of formula $(R^2)_2PYP(R^2)_2$ where the $R^2$ groups are independently selected from $C_1$ to $C_4$ alkyl, phenyl or alkoxy substituted phenyl, and Y is $-(CH_2)_n-$ where $n=2$ to 4 are provided. The complexes may be prepared by reacting the compounds $Pd(R'CO_2)_2$ and $(R^2)_2PYP(R^2)_2$ together in an aromatic solvent at a temperature of less than 60° C. in amounts such that the molar ratio of the two compounds is in the range 1.2:1 to 1:1.2.

5 Claims, No Drawings

PREPARATION OF PALLADIUM CATALYSTS

The present invention relates to the preparation of certain palladium carboxylate complexes which are useful sources of catalysts for the synthesis of linear alternating polymers of one or more olefins and carbon monoxide.

J Chem Soc 3632 (1965) discloses the preparation of palladium carboxylates by either reaction of palladium (II) nitrate with the corresponding carboxylic acid (e.g. acetic acid or propionic acid) or by an exchange reaction involving palladium (II) acetate and e.g. benzoic acid or trifluoroacetic acid. This paper also teaches that adducts of formula $Pd(CH_3CO_2)_2(PPh_3)_2$ or $Pd(C_2H_5CO_2)_2(PPh_3)_2$ (where Ph=phenyl) can be prepared by reacting the corresponding palladium carboxylate $Pd(CH_3CO_2)_2$ or $Pd(C_2H_5CO_2)_2$ with triphenylphosphine in benzene. These adducts however are said to dissociate and decompose rapidly in warm solvents.

In J Chem Soc Dalton (1982) 1109 palladium complexes of formula $Pd(O_2CPh)_2(PPh_3)_2$ and $Pd(O_2CPh)_2(Ph_2PCH_2CH_2PPh_2)$ are reported along with their physicochemical properties. These complexes are prepared by reacting the corresponding palladium (o) complexes $Pd(PPh_3)_4$ or $Pd(Ph_2PCH_2CH_2PPh_2)_2$ with dibenzoyl peroxide at room temperature.

EP 121965 and EP 181014 exemplify mixing palladium acetate with 1,3-bis(diphenylphosphine)propane in methanol in the molar ratio 1:1.5. The product of these reactions is however not a simple palladium complex of the type described above.

It has now been found that palladium complexes having the general formula $Pd(R'CO_2)_2X$ where R' is $C_1$ to $C_{10}$ alkyl or $C_6$ to $C_{10}$ aryl and X is a chelating ligand of formula $(R^2)_2PYP(R^2)_2$ where the $R^2$ groups are independently selected from $C_1$ to $C_4$ alkyl or phenyl or phenyl substituted with a polar group and Y is $-(CH_2)_n-$, where n=2 to 4, or a substituted derivatives thereof can of prepared by reacting the precursors $Pd(R'CO_2)_2$ and $(R^2)_2PYP(R^2)_2$ together in a suitable solvent. Furthermore, it is our belief that certain of these palladium complexes are new and we have determined that they are effective sources of catalysts for copolymerising mixtures of one or more olefins and carbon monoxide to produce polyketones.

According to the present invention there is provided palladium complexes having the general formula $Pd(R'CO_2)_2X$ where R' is $C_1$ to $C_{10}$ alkyl or $C_6$ to $C_{10}$ aryl and X is a chelating ligand of formula $(R^2)_2PYP(R^2)_2$ where the $R^2$ groups are independently selected from $C_1$ to $C_4$ alkyl or phenyl or phenyl substituted with a polar group and Y is $-(CH_2)_n-$, where n=2 to 4, with the proviso that when R' is phenyl at least one $R^2$ group is other than phenyl.

The palladium complexes of the present invention may be prepared in the form of the monohydrate in substantially pure crystalline form by the process which will be described further below.

As regards the chelating ligand X, it is preferred that this is such that the $R^2$ groups are either all methyl or all aryl with chelating ligands in which the $R^2$ groups are phenyl or phenyl groups which are $C_1$ to $C_4$ alkoxy substituted at the ortho position being most preferred. The Y group is most preferably selected from $-(CH_2)_3-$ and $-(CH_2)_4-$. It is preferred that R' is $C_1$ to $C_4$ alkyl.

The palladium complexes of the present invention are easily prepared by reacting the compounds $Pd(R'CO_2)_2$ and $(R^2)_2PYP(R^2)_2$ together is an aromatic hydrocarbon which is liquid at or below 60° C. Examples of such aromatic hydrocarbons include benzene, toluene, one or more of the isomers of xylene and mesitylene. If the palladium complex is to be isolated, rather than used in situ, it is preferable to avoid the use of solvent such as methanol since this causes slow reduction of the complex. The molar ratio of the two precursors should be in the range 1.2:1 to 1:1.2 and the reaction should be carried out at a temperature below 60° C. to prevent decomposition of the product to metallic palladium.

Using the precedure described above it will be found that the reactants will initially dissolve in the solvent but that as reaction proceeds the palladium complex will precipitate out. The palladium complex can be separated from the reaction medium at the end of the reaction period by filtration and washed with fresh solvent to produce analytically pure material. Recrystallisation of the crude product can thereafter be carried out if it is so desired.

The palladium complexes of the present are useful sources of catalysts for copolymerising mixtures of one or more olefins with carbon monoxide to produce linear polymers comprised of $-Z-$ and $-CO-$ units where Z is a divalent group corresponding to the particular olefin or olefins used. A preferred method of using such a complex comprises dissolving it in an aliphatic alcohol solvent such as methanol or ethanol together with 1 to 50 equivalents of an acid such as p-toluenesulphonic acid, trifluoromethanesulphonic acid trifluoroacetic acid or boroasalicylic acid and thereafter contacting the solution with one or more olefins, suitably $C_1$ to $C_{10}$ alpha olefins preferably e.g. ethylene, propylene or mixtures thereof, and carbon monoxide at a temperature in the range 20° to 200° C. and 1 to 100 bar gauge. Further details of this process can be found in for example EP 121965 and EP 181014 the contents of which are herein incorporated by reference.

The invention will now be illustrated by the following Examples.

EXAMPLE 1

Preparation of $Pd(CH_3CO_2)_2(Ph_2P(CH_2)_3PPh_2)$ $H_2O$

A filtered solution of 1,3-bis(diphenylphosphino)propane (1.85 g, 4.49 mmol) in toluene (100 cm$^3$) was added with stirring to a filterd solution of palladium (II) acetate (1.00 g, 4.46 mmol) in toluene (25 cm$^3$) over a period of five minutes. After stirring at room temperature for thirty minutes, the reaction medium was filtered and the filtrate washed with fresh toluene (10 cm$^3$). The filtrate was dried in vacuo to give the desired product as a pale yellow powder. Yield 4.497 g (88%) $^1$H NMR (CH$_3$OD solvent): 7.3-8.1 (20H, m), 2.8-3.1 (4H, m), 2.1-2.4 (2H, m), 1.5 (6H, s). IR (KBr disc): $V_{asym}$(OCO)=1585 cm$^{-1}$, $V_{sym}$(OCO)=1372 cm$^{-1}$.

Elemental analysis: Found: C, 56.7; H, 5.3. Calculated for $C_{31}H_{34}O_5P_2Pd$: C, 56.8; H 5.2.

EXAMPLE 2

Use of the Complex in Preparing Polyketones

A carbon monoxide/ethene/propene terpolymer polyketone was prepared by the following method.

The precursor palladium complex of Example 1 (0.0131 g, 0.0207 mmol), together with 1,4-benzoquinone (0.3525 g 3.264 mmol), hydrogen bis(5- chlorosalicylato) borate (0.5207 g, 1.404 mmol), propylene (28.60 g, 0.68 mol) and methanol (100 cm$^3$) were mixed in a 300 cm$^3$ mechanically stirred autoclave. An equimolar mixture of ethylene and carbon monoxide was introduced such that the overall pressure was 33 bar g. The contents of the autoclave were brought to 50° C. and the overall pressure adjusted to 50 bar g. These conditions were maintained for four hours by addition of more of the gaseous mixture as appropriate. The polymerisation reaction was terminated by releasing the pressure. The polymer produced was collected by filtration, washed with acetone and dried in vacuo.

A yield of 11.3413 g of terpolymer polyketone was obtained.

I claim:

1. Palladium complexes in substantially pure crystalline form having the general formula Pd(R'CO$_2$)$_2$X where R' is C$_1$ to C$_{10}$ alkyl to C$_6$ to C$_{10}$ aryl and X is a chelating ligand of formula (R$^2$)$_2$PYP(R$^2$)$_2$ where the R$^2$ groups are independently selected from C$_1$ to C$_4$ alkyl, phenyl or phenyl substituted with a polar group, and Y is —(CH$_2$)$_n$— where n=3 or 4 with the proviso that when R' is phenyl at least one R$^2$ group is other than phenyl.

2. Palladium complexes as claimed in claim 1 wherein at least one R$^2$ group is a phenyl group which is C$_1$ to C$_4$ alkoxy substituted at the ortho position.

3. Palladium complexes as claimed in claim 2 wherein R$^1$ is C$_1$ to C$_4$ alkyl.

4. A process for preparing a palladium complex having the general formula Pd(R'CO$_2$)$_2$X where R' is C$_1$ to C$_{10}$ alkyl or C$_6$ to C$_{10}$ aryl and X is a chelating ligand of formula (R$^2$)$_2$PYP(R$^2$)$_2$ where the R$^2$ groups are independently selected from C$_1$ to C$_4$ alkyl, phenyl or phenyl substituted with a polar group and Y is —(CH$_2$)$_n$ where n=2 to 4 which process comprising reacting the compounds Pd(R'CO$_2$)$_2$ and (R$^2$)$_2$PYP(R$^2$)$_2$ together is an aromatic solvent at temperature of less than 60° C. in amounts such that the molar ratio of the two compounds is in the range 1.2:1 to 1:1.2.

5. A process as claimed in claim 4 wherein the aromatic solvent is selected from benzene, toluene, one or more of the isomers of xylene and mesitylene.

* * * * *